United States Patent [19]
Schiff

[11] 3,960,937
[45] June 1, 1976

[54] ASHLESS ADDITIVES FOR LUBRICATING COMPOSITIONS

[75] Inventor: Sidney Schiff, Bartlesville, Okla.

[73] Assignee: Phillips Petroleum Company, Bartlesville, Okla.

[22] Filed: May 4, 1972

[21] Appl. No.: 250,292

Related U.S. Application Data

[63] Continuation-in-part of Ser. No. 160,499, July 7, 1971, abandoned.

[52] U.S. Cl............ 260/501.2; 260/504 R; 260/501.21; 252/33; 252/33.2
[51] Int. Cl.²............ C07C 87/14; C07C 87/20
[58] Field of Search ........... 260/501.2, 504; 252/33, 252/33.2

[56] References Cited
UNITED STATES PATENTS

| | | | |
|---|---|---|---|
| 2,680,716 | 6/1954 | Lipkin et al. | 260/504 R X |
| 2,726,261 | 12/1955 | Martin | 260/504 R |
| 2,807,589 | 9/1957 | Mitchell et al. | 260/504 R X |
| 2,989,564 | 6/1961 | Ambrose et al. | 252/33.2 X |
| 3,025,240 | 3/1962 | Sheldahl | 252/33 |
| 3,189,544 | 6/1965 | Ratner et al. | 252/33 |
| 3,367,864 | 2/1968 | Elliott et al. | 252/33 |
| 3,401,117 | 9/1968 | Schiff | 260/504 R X |
| 3,634,241 | 1/1972 | Lowe | 252/33 |

*Primary Examiner*—James O. Thomas, Jr.
*Assistant Examiner*—G. Breitenstein

[57] ABSTRACT

Superior ashless additives for lubricants are prepared by a process comprising first introducing a petroleum sulfonic acid and a polyamine to a reaction zone and subsequently introducing a cyclic anhydride of a dicarboxylic acid into the reaction zone. In another embodiment, the solids content of the additives is reduced to acceptable levels by removal of free $SO_2$ from the petroleum sulfonic acid prior to preparing the additive. Lubricating oil compositions containing these ashless additives are also provided.

11 Claims, No Drawings

ASHLESS ADDITIVES FOR LUBRICATING COMPOSITIONS

BACKGROUND OF THE INVENTION

This is a continuation-in-part application of my co-pending application having Ser. No. 160,499, filed July 7, 1971, now abandoned entitled "Ashless Additives for Lubricating Compositions."

This invention relates to improved ashless additives for lubricating compositions. Another aspect of this invention relates to a process for the preparation of the improved ashless additives. In accordance with another aspect, this invention relates to the preparation of ashless dispersants for lubricants having reduced solids content made from petroleum sulfonic acids which have been treated to remove free $SO_2$ prior to preparation of the dispersant. In a further aspect, this invention relates to lubricating compositions containing said improved additives.

At the present time it is common practice to enhance or modify certain of the properties of lubricating oils through the use of various additives or improvement agents. The lubricating oils employed in internal combustion engines, such as automotive, light aircraft and diesel engines, in particular, require the use of additive agents to render them serviceable under the adverse environmental conditions frequently encountered in the operation of these engines. Among the various additives employed in modern engine oils, one of the most important is the type which acts to prevent an accumulation of sludge in the crank case and on the cylinder walls, thereby preventing sticking of the piston rings and the formation of varnish-like coatings on the pistons and cylinder walls. Because of their general function of maintaining a clean engine, additives of this nature are termed "detergents" although it is now understood that they have little utility in cleaning a dirty engine, but, by virtue of dispersant activity, prevent or greatly retard engine fouling.

Metal petroleum sulfonates have been widely used as detergent additives for lubricating oils. Since they contain metals, these conventional additives form ash deposits in the engine when added to motor oil or, when added to oil which is mixed with gasoline in 2-stroke engines, form deposits which foul spark plugs. These deposits contribute to pre-ignition and overall lower engine performance and engine operating efficiency. Therefore, it is desirable to discover new additives having superior detergent qualities such as are possessed by the metal containing additives that, however, avoid the presence of the ash forming metal. Such additives are referred to as being ashless. An "ashless" detergent may be more particularly characterized as one which shows substantially no ash when tested by ASTM procedure D-482-59T.

An object of this invention is to provide superior ashless additives for lubricating compositions. Another object of this invention is to provide a process preparing the ashless additives. Another object of this invention is to provide an improved lubricating composition containing said superior ashless additives. A further object of this invention is to provide ashless dispersants for lubricants having reduced solids content.

DESCRIPTION OF THE PREFERRED EMBODIMENT

Now in accordance with the present invention I have discovered that effective, but ashless, additives having excellent detergent properties, when compounded with a lubricating oil, can be obtained by first introducing a petroleum sulfonic acid and a polyamine to a reaction zone, allowing them to interact, and then introducing to the reaction zone a cyclic anhydride of a dicarboxylic acid. This invention, then, involves the process by which these superior additives are obtained, the additives themselves, and the lubricant compositions in which they can be employed.

Further in accordance with the invention, the solids content of ashless additives for lubricants made from petroleum sulfonic acids is reduced to acceptable levels by removal of free $SO_2$ from the sulfonic acid oil used in preparing the additive. It has been found that it is desirable, in making an ashless dispersant or additive for lubricant formulations, to maintain a low level of centrifugable solids. Thus, by maintaining a low concentration of free $SO_2$ in the petroleum sulfonic acid prior to formation of the additive, this results in an additive having a low solids content which improves the visual appearance of the additive, minimizes deposits that build up during engine operation, and offers an economic advantage of not requiring a costly process step to remove solids from the product.

It is preferred to use a petroleum sulfonic acid having a maximum of about 0.15 weight percent free $SO_2$ in the oil so as to produce a lubricating oil additive having a low solids content. The petroleum sulfonic acid can have initially no more than about 0.15 weight percent free $SO_2$ or can be one that has been treated to reduce the free $SO_2$ content of the oil to about 0.15 weight percent or less.

Generally speaking, any petroleum sulfonic acid prepared in accordance with methods known in the art can be employed in this invention. For example, U.S. Pat. No. 3,135,693 describes a method of making metal petroleum sulfonates in which a petroleum sulfonic acid is prepared as an intermediate.

A wide variety of oils can be used as the charge oils in preparing the petroleum sulfonic acids of this invention. Preferably, the charge oil is selected from viscous oil fractions of petroleum having a viscosity of at least 50 SUS at 210°F. The upper viscosity limit for these viscous oil fractions would be about 720 SUS at 210°F.

Sulfonating agents which are known to the art can be utilized in the sulfonation step preparing these petroleum sulfonic acids. Sulfonating agents which can be so used include fuming sulfuric acid and liquid sulfur trioxide. Said fuming sulfuric acid can vary from 10 weight percent to 40 weight percent excess sulfuric trioxide. However, when sulfuric acid is used, it is usually preferred to use commercial fuming sulfuric acid which contains about 20 weight percent sulfur trioxide. Liquid sulfur trioxide, i.e., liquid sulfur trioxide in liquid sulfur dioxide, is the presently preferred sulfonating agent for use in preparing the petroleum sulfonic acids used in the practice of this invention. Such liquid sulfur trioxide is commercially available.

When 20 percent fuming sulfuric acid is used as the sulfonating agent, the acid-oil ratio can be in the range of from about 0.1:1 to about 0.7:1, or even 1:1 to produce the petroleum sulfonic acids used in the practice of the invention. A preferred range of acid-oil ratios is in the range of about 0.3 to about 0.6:1. When liquid sulfur trioxide in liquid sulfur dioxide is the sulfonation agent, the sulfur trioxide to oil weight ratios are maintained equivalent to those available from the 20 percent fuming sulfuric acid values given above. In other words, the sulfur trioxide to oil ratio can be in the range of about 0.02 to 0.2, preferably from about 0.06 to about 0.12:1. Said sulfur trioxide to oil ratios can be controlled by varying the rate of flow of the oil or the sulfur trioxide containing medium, or both. The above given ratios are weight ratios.

Sulfonation temperatures can be controlled within the range of about 50° to about 200°F with the preferred operating range between about 80° and about 150°F. At temperatures above about 200°F, excessive oxidation with liberation of sulfur dioxide may take place. A reaction time of about 20 to about 90 minutes is preferred when fuming sulfuric acid is utilized as the sulfonating agent in order to provide optimum yield and quality of products. When sulfur trioxide, e.g., sulfur trioxide and sulfur dioxide, is utilized as the sulfonation agent, the reaction rate is greatly accelerated and the reaction has been found to be substantially completed in the time required to accomplish suitable contact of the oil with the sulfur trioxide, usually less than about 5 minutes. The sulfonation reaction can be varied out at atmospheric pressure although pressures greater or less than atmospheric can be employed, if desired. When using liquid sulfur trioxide in liquid sulfur dioxide as the sulfonating agent, it is preferred to carry out the reaction at sufficient pressure to maintain the sulfur dioxide in liquid phase.

In the actual practice of this invention, the petroleum sulfonic acid can be prepared in situ and used after removal of residual $SO_2$ and sulfonating agent in the preparation of the ashless additives of this invention. Alternatively, the petroleum sulfonic acid employed can be derived from some other source. The residual $SO_2$ present in the petroleum sulfonic acid can be removed in any desired manner. One procedure that can be employed involves stripping of the sulfonated oil with an inert gas under conditions such that free $SO_2$ will be removed from the oil along with the inert gas. The inert gas and $SO_2$ can be separated if desired, following stripping of the sulfonated oil. Suitable inert gases include nitrogen, argon, neon, and the like. In one preferred embodiment, the finished sulfonated oil is treated by bubbling nitrogen or other inert gas at a temperature between about 80°–100°F for about one to three hours or until a sample analysis shows that the free $SO_2$ in the oil has been reduced to about 0.15 weight percent or less. It is also within the scope of the invention to strip free $SO_2$ from the oil by thin film evaporation under reduced pressure (vacuum).

It is within the scope of this invention to use any cyclic anhydride of a dicarboxylic acid. However, those cyclic anhydrides generally employed are preferably derived from diacids having 4 to 20 carbon atoms. As will be appreciated by those skilled in the art, commercial availability, ease of synthesis, and economic factors rather than theoretical limitations are the most significant considerations upon which this preferance is based.

Examples of suitable cyclic anhydrides that can be used in this invention include maleic anhydride and substituted maleic anhydrides wherein the substituents are selected from hydrocarbyl groups having from 1 to 6 carbon atoms. Such anhydrides can be represented by the formula

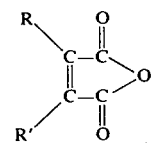

wherein R and R' can be the same or different and are selected from the group consisting of a hydrogen atom and cyclic, acyclic and aromatic hydrocarbyl groups having 1 to 6 carbon atoms. Examples of said maleic anhydrides include, among others, the following:
maleic anhydride,
methyl maleic anhydride (citriconic anhydride),
ethyl maleic anhydride,
butyl maleic anhydride,
cyclobutyl maleic anhydride,
hexyl maleic anhydride,
cyclohexyl maleic anhydride,
dimethyl maleic anhydride,
methyl ethyl maleic anhydride,
ethyl cyclohexyl maleic anhydride,
phenyl maleic anhydride,
methyl phenyl maleic anhydride,
and the like.

Still other examples of suitable cyclic anhydrides include the cyclic anhydrides derived from saturated diacids. Of this type the cyclic anhydrides of succinic acid and substituted succinic acids of the formula

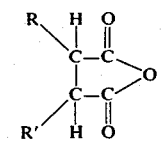

wherein R and R' are as defined above and can be the same or different are representative. Examples of these cyclic anhydrides include, among others, the following:
succinic anhydride,
methyl succinic anhydride,
butyl succinic anhydride,
cyclobutyl succinic anhydride,
hexyl succinic anhydride,
cyclohexyl succinic anhydride,
dimethyl succinic anhydride,
ethyl cyclohexyl succinic anhydride,
phenyl succinic anhydride,
methyl phenyl succinic anhydride,
and the like.

Still other examples of suitable cyclic anhydrides are those of aromatic diacids. Representative of these are the cyclic anhydrides derived from phthalic acids and its derivatives of the formula

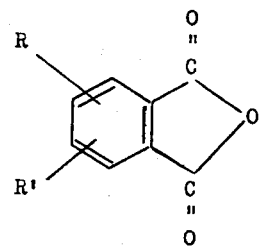

wherein R and R' are as defined above and can be the same or different. Examples of such anhydrides include, among others, the following:
  phthalic anhydride,
  3-methyl phthalic anhydride,
  4-methyl phthalic anhydride,
  3-propyl phthalic anhydride,
  3-hexyl phthalic anhydride,
  4-cyclohexyl phthalic anhydride,
  4-phenyl phthalic anhydride,
  3,4-dimethyl phthalic anhydride,
  3-methyl-4-hexyl phthalic anhydride,
  3-ethyl-4-phenyl phthalic anhydride,
  3,5-dimethyl phthalic anhydride,
  3,6-dimethyl phthalic anhydride,
  3-methyl-5-ethyl phthalic anhydride,
  3-methyl-6-hexyl phthalic anhydride,
  and the like.

A wide variety of polyamines can be used in the practice of this invention. One class of suitable polyamines can be represented by the formula

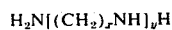

wherein $x$ equals 2–6 and $y$ equals 1–100. Examples from this class of suitable polyamines which can be used in the practice of the invention include, among others, the following:
  ethylenediamine,
  diethylenetriamine,
  triethylenetetramine,
  tetraethylenepentamine,
  dipropylenetriamine,
  butylenediamine,
  hexamethylenediamine,
  tetrahexylenepentamine,
  heptabutyleneoctamine,
  and the like.

A second class of suitable polyamines comprises the polymers of 1,2-alkylene imines. Polyalkylene imines can be derived from the acid (e.g., small amount of HCl) catalyzed polymerization of 1,2-alkylene imines of the formula

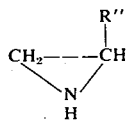

and are polyamines of the general formula $(C_2H_4R'\lambda'N)_n$ wherein n represents the average degree of polymerization and R'' is selected from hydrogen and alkyl radicals having one to 14 carbon atoms such as methyl, ethyl, butyl, tetradecyl, and the like. Polymerized 1,2-alkylene imines of essentially any degree of polymerization ($n$ value) may be used.

Because of its commercial availability over a wide range of molecular weights, a presently preferred polyalkylene imine is polyethylenimine (R''=H). Polyethylenimine, obtained by the acid catalyzed polymerization of ethylene imine, contains a random distribution of primary amino groups of the formula —CH$_2$CH$_2$NH$_2$, secondary amino groups of the formula

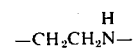

and tertiary amino groups of the formula

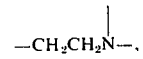

in the approximate ratio of one primary amino group: two secondary amino groups: one tertiary amino group. One specific polyethylenimine that can be employed in this invention has an average molecular weight of about 1,800 and an average degree of polymerization of about 42. A commercially available polyethylenimine corresponding to a molecular weight of about 1,800 is PEI 18, available from the Dow Chemical Company of Midland, Mich. PEI 18, as obtained commercially, is substantially anhydrous. This is a desirable feature in that the presence of water in the reaction medium is undesirable at the time the cyclic anhydride is added since water will tend to compete with the polyamine for reaction with the anhydride and, if successful, regenerate the diacid from which the cyclic anhydride was derived.

It is within the scope of this invention to use a mixture of polyamines wherein the mixture includes more than one member from the same class or members from each class.

Other methods of preparing the polyalkylene imines useful in this invention include the reaction of alkylene dichlorides with ammonia and the thermal decarboxylation of 2-oxazolidones.

In the preparation of the ashless detergent of this invention a two-stage process is employed. In the first stage, the petroleum sulfonic acid, with or without prior treatment to reduce free SO$_2$ content, and the polyamine are introduced to a reaction zone. The two reactants can be introduced simultaneously or in whatever sequence desired. When sufficient time has elapsed to insure completion of this reaction, as a second stage the specific cyclic anhydride being used is introduced to the reaction zone.

In this process for the preparation of the ashless detergent a wide range of reaction conditions can be employed.

The two stages of the process can be conducted in the presence or absence of a diluent as desired. If a diluent is employed, it may be added alone or as a solvent for one or more of the reactants. To be suitable a diluent need only be inert under the reaction conditions used. Preferred solvents include volatile hydrocarbon liquids having from 5 to 12 carbon atoms per molecule and are selected from alkanes, cycloalkanes, aromatics, and alkyl aromatics or mixtures thereof. Examples of these are hexane, heptane, cyclohexane, benzene, toluene, ethyl benzene, paraxylene, and the like. Also suitable as solvents for this reaction are lube oil stocks having 100°F viscosities up to 150 SUS. A preferred lube oil stock has a 100°F viscosity of about 100 SUS. Volatile solvents are preferred because of the convenience of their removal during the process of recovering the desired ashless additive. The lube oil stocks are preferred in those circumstances when it is desirable to recover the additive in an oil base. In this form it can be conveniently used for blending purposes with a lubricant into which it will ultimately be incorporated. It is also within the scope of this invention to use mixtures of solvents wherein both a volatile solvent and a lube oil stock are used in combination as reaction diluents.

Inasmuch as the initial reaction likely involves the interaction of each molecule of petroleum sulfonic acid with one of the amine groups in the polyamine to form a salt of the formula $R''' - SO_3^- HN^+\leqslant$ wherein $R'''$ is an organic radical representative of the oil stock from which the petroleum sulfonic acid is derived, it will be appreciated by those skilled in the art that a wide range of temperatures can be employed in this stage of the process. All that is required is that the reaction mixture remain fluid enough that mixing is not hampered and that temperatures sufficiently high to cause decomposition be avoided. Temperatures from about room temperature to about 300°F are usually suitable. As a practical consequence of the fact that the reaction is exothermic, the temperature is usually moderated by cooling means to avoid excessive heating.

It is believed that the interaction between the petroleum sulfonic acid and the polyamine is essentially instantaneous, i.e., reaction takes place about as fast as mixing. Therefore, stirring or other means of agitating the reaction mixture should be maintained without additional process steps for a period of time sufficient to insure that mixing and hence reaction is complete. Generally, at least about 5 minutes are allowed to elapse to insure complete mixing.

After the time allotted for the reaction of the petroleum sulfonic acid and polyamine has elapsed, the desired cyclic anhydride is introduced to the reaction zone. Generally, this stage of the reaction can be conducted over a wide temperature range from about room temperature to about 300°F. As in stage 1, it is desired to maintain the reaction in a sufficiently fluid state so as to not hamper mixing and to avoid temperatures so high as to be deleterious. Elevated temperatures varying from 100° to 250°F are preferred.

When a volatile solvent is employed in either or both of the stages of the process described above, the temperature at which reflux occurs will usually be that employed. In both the first and second stage of the process, the respective reactions can be sufficiently rapid and exothermic so as to require cautious addition to prevent an abrupt increase in reaction temperature.

The reaction with the cyclic anhydride is thought to involve the residual primary or secondary amine groups of the polyamine not neutralized by the petroleum sulfonic acid in the first stage of the process. The product of this reaction may, initially, be an amide corresponding to Formula A below:

Formula A

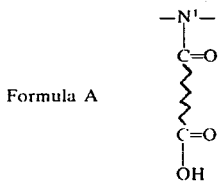

wherein

in Formula A is a secondary or tertiary amine group. This group was present as a primary or secondary amine group in the polyamine and had not previously interacted with the petroleum sulfonic acid. Formula B, as set out below, is representative of a more specific example corresponding to the general Formula A wherein the cyclic anhydride employed is maleic anhydride or a derivative thereof.

Formula B

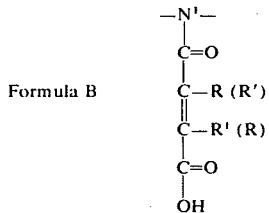

R and R' are as defined above.

Since water is liberated during the reaction, it is believed that the free acid end of the intermediate amide as shown in Formulas A or B above must be at least partially involved in a further acylation with unreacted amine groups to produce amides. This may involve an intermolecular cross-linking acylation to join two polyamines as shown in the Formulas C and D as set out below:

Formula C 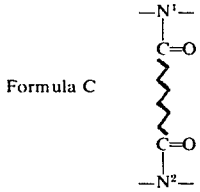   Formula D 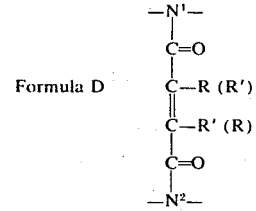

wherein

and

in Formulas C and D represent secondary or tertiary amine groups in separate polyamine molecules. Alternatively, the acylation reaction involving the free acid end may take place at an adjacent amine group of the same polyamine to form an intramolecular cyclic amide structure as shown in Formulas E and F as set out below:

Formula E              Formula F

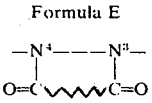     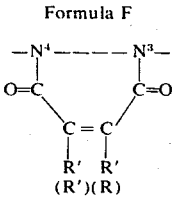

wherein

and

in Formulas E and F represent secondary or tertiary amine groups and at least one is a tertiary amine group on the same polyamine chain. However, it is not known to what extent these reactions occur nor which course is preferred.

Being exothermic, as pointed out above, the reaction involving the cyclic anhydride is quite rapid. Therefore, the time allotted for this reaction may vary over a wide range. Generally, it is preferred to use a contacting time of from 5 minutes to about 1 hour to insure that substantially complete reaction has taken place.

The order of addition of the reactants, as described above, is an important feature of this invention. By first allowing the polyamine to interact with the petroleum sulfonic acid, primary amine groups are thought to be neutralized in preference to secondary amine groups (or tertiary amine groups if present in the polyamine employed). Therefore, when the desired cyclic anhydride is added to the reaction zone, it reacts with unreacted primary amine groups, if any, and secondary amine groups. Of course, tertiary amine groups are incapable of forming amides by interacting with the cyclic anhydride.

The quantities of reactants used in this invention are most conveniently expressed in chemical equivalents.

One equivalent of the petroleum sulfonic acid is that amount in grams of acid oil which would contain sufficient sulfonic acid groups to neutralize one mole of an alkali metal base such as sodium hydroxide wherein a salt and water are formed (i.e., $R'''SO_3H + NaOH \rightarrow R'''SO_3Na + H_2O$).

A practical method for determining the extent of sulfonation of a petroleum sulfonic acid (and hence the equivalent weight) comprising neutralizing the acid oil with a base and titration with a standard solution of cetyl pyridinium bromide, using methylene blue as an indicator, is described in U.S. Pat. No. 3,135,693. While the equivalent weight may vary according to the degree of sulfonation, petroleum sulfonic acids used in the examples forming a part of this application will have an equivalent weight of the order of 2,000 grams or, stated alternatively, 0.5 milliequivalents per gram of petroleum sulfonic acid.

Each mole of polyamine will have as many equivalents of amine as there are amine groups per molecule. However, for this invention it is necessary to determine only the equivalents per mole of primary and secondary amine groups. For example, ethylenediamine has two equivalents of primary amine per mole, diethylenetriamine has two equivalents of primary amine and one equivalent of secondary amine per mole, etc.

When the polyamine is a polyethylenimine, of the amine groups present per average molecule, about 25 percent are primary, about 50 percent are secondary, and about 25 percent are tertiary amine groups. Therefore, if the average molecular weight is 1,800, the average molecule will have 42 repeating units and of these about 10.5 (25 percent of 42) will be primary, and 21 (50 percent of 42) will be secondary amine groups. Thus, one mole of a polyethylenimine having a molecular weight of 1,800 will have 10.5 equivalents of primary imine and 21 equivalents of secondary amine.

In order to determine the equivalents of primary or secondary amine to be employed it is only necessary to multiply the moles of polyamine being used (number of moles equals actual weight of polyamine divided by the molecular weight) by the number of primary or secondary amine groups per molecule.

The equivalents of the cyclic anhydride employed is based on the formula weight. Therefore, for example, one equivalent of maleic anhydride itself is 98.02 grams which is also the formula weight.

The amount of petroleum sulfonic acid employed in this invention should be sufficient to neutralize not less than about 10 percent of the total equivalents of primary and secondary amine present in the amount of polyamine employed and should not exceed an amount sufficient to neutralize about 75 percent of the total equivalents of primary and secondary amine, with the further proviso that not less than one equivalent of petroleum sulfonic acid per mole of polyamine should be employed in every case. This can be expressed as a range from 1 equivalent per mole to 0.75 A, wherein A represents the total equivalents of primary and secondary amines present in the amount of polyamine employed. Best results are obtained over a range from 0.15 A to 0.65 A.

The equivalents of the cyclic anhydride employed may vary over the range from 0.25 (A–E) to A–E, wherein A is as defined above and E is the equivalent of petroleum sulfonic acid employed. Lower levels of cyclic anhydride are used when it is desired to increase the intra- and intermolecular amide formation resulting from a subsequent reaction of the carboxylic acid residue obtained after the initial reaction of the cyclic anhydride with polyamine as is described above. Best results are obtained when the equivalents of anhydride employed varies from 0.35 (A–E) to 0.75 (A–E).

Several different methods of recovering the product additive from the reaction mixture can be employed. The particular additive recovery method employed will depend to some extent on the method employed for interacting the petroleum sulfonic acid, polyamine, and the anhydride. It is desirable that essentially all the water formed during the reaction or reactions, or which is otherwise present, be removed at some stage of the recovery process. This can be done in any suitable manner. One method is to add to the reaction mixture a chemically inert diluent which is capable of forming an azeotrope with water, and then refluxing the diluted reaction mixture under azeotropic distillation conditions to remove a diluent-water azeotrope. After the water has been removed, the remaining azeotrope forming diluent is removed from the reaction mixture by distillation, preferably vacuum distillation. If desired, the diluent can be employed as a diluent or solvent for one or more of the reactants and can be present in the reaction zone during the reaction or reactions. Thus the diluent can be added along with one of the reactants or a reactant can be dissolved in the diluent and the resulting solution added to the other reactant or reactants. Any azeotrope forming diluent which is chemically inert, i.e., does not react chemically with the petroleum sulfonic acid, the polyamine, or the anhydride, or the reaction product thereof can be used in the practice of this invention. A presently preferred azeotrope forming diluent is benzene.

If desired, the water can be removed from the reaction mixture by blowing the heated reaction mixture, e.g., at a temperature within the range of from 220° to 300°F for a period of time within the range of from 0.5 to 2 hours, with an inert gas such as nitrogen, helium, argon, krypton, neon, xenon, or mixtures thereof.

Insoluble, finely divided solids can be removed from the reaction product by filtration. This filtration is best accomplished by using a filtering aid such as Celite. However, as pointed out above, this step is unnecessary and can be avoided when employing petroleum sulfonic acids having less than about 0.15 weight percent free $SO_2$ prior to formation of the additive. As is demonstrated by the examples hereinbelow, the solids content of the reaction product is minimal when the free $SO_2$ concentration in the petroleum sulfonic acid is at a desirably low concentration.

If a volatile solvent is employed in the reaction, it is removed by distillation. To facilitate removal it is preferred to perform the distillation at reduced pressure by well-known vacuum stripping techniques. The pressure at which this is done may vary over a wide range, but generally will be below about 20 millimeters of mercury pressure. Any excess azeotrope forming diluent previously added may also be removed at this time.

If desired, the product additive of the invention can be recovered as a solution or other dispersion in a light lubricating oil blending stock. One manner in which this may be done is to use the lube oil blending stock as the reaction solvent for preparation of the additive. This has the advantage of eliminating the requirement for removing the volatile solvent as described above.

If a volatile solvent is used in the preparation of the product additive, the lubricating oil blending stock can be added to the reaction mixture, preferably after the removal of the water but prior to removal of the volatile solvent therefrom. Alternatively, the lubricating oil blending stock can be added to the reaction mixture after the removal of the volatile solvent.

The product additives of this invention, either alone or as a solution or other dispersion in light lubricating oil blending stock such as described above, can be incorporated into lubricating oil compositions in several combinations depending upon specific service requirements. For example, if desired and particularly in the case of heavy duty oils, such as those used in trucks, buses, and general diesel applications, the concentrated additive of this invention can be blended with suitable lubricating oil base stocks. In many general duty crankcase oils, the product additive as a solution or dispersant in the lube oil blending stock can be blended with appropriate base oils. In these variations of blending, the additives of this invention will provide high quality lubricating oils as required in various ordnance and other qualification tests and other specifications, and outstanding performance with respect to sludge formation in stop-and-go engine operation. As already noted, the absence of metallic salts in the product additive of this invention has the added advantage of making them ash-free.

Generally speaking, product additives of this invention, prepared according to the processes described above, can be added to the base lubricating oil in an amount sufficient to obtain the desired degree of improved characteristics of the base oil. Said product additives can be added to said base oil in amounts of about 0.2 to about 30 weight percent of the finished oil. The concentration of the petroleum sulfonic acid-polyamine-cyclic anhydride reaction product alone is normally in the range of about 0.1 to about 15 weight percent of the finished oil since a portion of the product additive is unsulfonated oil. A presently preferred concentration of said product additive comprising petroleum sulfonic acid-polyamine-cyclic anhydride reaction product and unsulfonated oil is in the range of 2 to 20 weight percent of the finished oil. A presently preferred concentration of the petroleum sulfonic acid-polyamine-cyclic anhydride reaction product in the finished oil is in the range of about 1 to about 10 weight percent of the finished oil. In addition to the product additives of this invention, the finished oil may contain other additives which are normally incorporated into lubricating oil compositions without deleterious effect.

The following examples will serve to further illustrate the process and utility of this invention.

EXAMPLE I

A 1,100 gram quantity of a Camrick-Ellenburger lubricating oil blending stock* was dissolved in 1,900 milliliters of cyclohexane. Liquid sulfur trioxide (55 grams) was allowed to vaporize and be swept by nitrogen stream into the reaction vessel. The temperature was maintained between 75° and 80°F. by controlling the rate of addition and using external cooling means. Stirring was maintained during the addition (40 minutes) and continued for an additional 20 minutes.

*Viscosity 210°F=108.7 SUS; at 100F, 1283 SUS.

The petroleum sulfonic acid oil was decanted into a reaction vessel. A 100 gram quantity of polyethylenimine having a molecular weight of about 1,800 (PEI 18, manufactured by the Dow Chemical Company of Midland, Mich. was introduced to the reaction vessel. Rapid stirring was used to facilitate mixing. The color of the mixture changed from black to brown, indicative of complete reaction of the petroleum sulfonic acid. The temperature rose from 75° to 93°F.

The reaction mass was heated to reflux and maleic anhydride (60 grams) was added. After addition was completed, 200 milliliters of benzene were added and a water-benzene azeotrope removed.

The resulting mixture was filtered through Celite, to remove a small amount of sludge, and a quantity of light lube oil blending stock (200 grams) was added and the solvent stripped off in a vacuum (16 millimeters) at 250°F. This resulted in a base stock material having 86 percent of the product additive in the lubricating oil blending stock.

The product of Example I was subjected to standard automotive Sequence VB test (ASTM Special Technical Publication No. 315-C) and compared with a commercial additive.

|  | Trop-Artic[a] with 1.35% Product I | Trop-Artic[a] with 1.6% Lubrizol 925[b] |
|---|---|---|
| Overall Sludge (50 = Clean) | 45.0 | 45.7 |
| Overall Varnish (50 = Clean) | 42.2 | 34.5 |

|  | Trop-Artic[a] with 1.35% Product I | Trop-Artic[a] with 1.6% Lubrizol 925[b] |
| --- | --- | --- |
| Piston Varnish (10 = Clean) | 9.6 | 9.0 |
| Oil Screen Plugging, % | 1 | 1 |
| Oil Ring Plugging, % | 0 | 1 |

[a] A registered trademark of the Phillips Petroleum Company representing SAE 10W-30 oil containing calcium petroleum sulfonate, oxidation inhibitor and viscosity index improver.
[b] Ashless nitrogenous additive made by Lubrizol Corp. of Cleveland, Ohio (concentration of ashless additive set to yield same N concentrate in final blend).

This comparison test shows the improvement obtained by using a product additive of this invention when compared to a commercially available additive.

EXAMPLE II

A sulfonated petroleum oil made from a lubricating oil stock (viscosity 210°F about 200 SUS) (1,200 grams) in 1,200 grams of a light lubricating oil blending stock was contacted with polyethylenimine (168 grams) having an average molecular weight of 1,800 (PEI 18, manufactured by the Dow Chemical Company of Midland, Michigan) for 1 hour at 235°F. Maleic anhydride (100 grams) was introduced causing the temperature to rise to 259°F. The reaction mixture was maintained at 250°F for ½ hour and nitrogen was bubbled therethrough. The resulting mixture was allowed to cool to room temperature.

A comparison was made of the product of the invention of Example II with an experimental material prepared without the maleic anhydride treatment using the Sequence VB tests with the following results:

|  | Trop-Artic[a] with Product II | Trop-Artic[a] with Experimental Material made Without Maleic Anhydride |
| --- | --- | --- |
| Overall sludge | 40.4 | 33 |
| Overall Varnish | 42.3 | 37 |
| Piston Varnish | 8.8 | 9.4 |
| Oil Screen Plugging, % | 10 | 30 |
| Oil Ring Plugging, % | 1 | 2 |

[a] A registered trademark of the Phillips Petroleum Company representing an SAE 10W-30 oil containing calcium petroleum sulfonate, oxidation inhibitor and viscosity index improver.

This shows the improvement which is made by treating the amine sulfonate product with an anhydride. The experimental additive made without maleic anhydride was prepared by contacting with stirring 1,000 grams of the sulfonated petroleum oil of this example, in benzene, with 60 grams of polyethylenimine having an average molecular weight of 1,800 (PEI 18, manufactured by the Dow Chemical Company). The product was purified by filtration through Celite followed by the addition of 333 grams of light lube oil blending stock and vacuum distillation of the solvent. The resultant base stock material contained 75.8 percent additive in the lube oil blending stock.

EXAMPLE III

Sulfonated petroleum oil as in Example II (60 grams) and diethylenetriamine (2.5 grams) were stirred under nitrogen at 300°F for 30 minutes. Maleic anhydride (3.0 grams) was introduced to the reaction zone and stirred at 450°F for 40 minutes. Some decomposition was observed at 450°F. The reaction mixture was then cooled to 150°F, diluted with cyclohexane and filtered through Celite. A light lubricating oil blending stock (20 grams) was then added and the solvent stripped by vacuum distillation. This resulted in a base stock material having 64.6 percent of the product additive in the lubricating oil blending stock. Because of the observed decomposition, a lower operating temperature is preferred.

EXAMPLE IV

A solution of sulfonated petroleum oil as in Example II in light lube oil blending stock (2,127 grams of a 59 percent solution) was added with stirring to a mixture of tetraethylenepentamine (96 grams) and light lube oil blending stock (360 grams). During the reaction the temperature increased from 74°F to 109°F. This temperature was then raised to 162°F and maleic anhydride (72 grams) added. The temperature rose to 176°F and was blown with nitrogen at this temperature for one hour.

The product of Example IV was subjected to a Sequence VB test.

|  | Trop-Artic with Product of Example IV |
| --- | --- |
| Overall Sludge (50 = Clean) | 45.5 |
| Overall Varnish (50 = Clean) | 39.7 |
| Piston Varnish (10 = Clean) | 9.4 |
| Oil Screen Plugging, % | 0 |
| Oil Ring Plugging, % | 0 |

The product of Example IV was subjected to a standard Caterpillar 1-H test (MIL-L-2104B) and compared with a commercial additive.

|  | Trop-Artic[a] with Product of Example IV | Trop-Artic[a] with Lubrizol 925[b] |
| --- | --- | --- |
| Topgroove Carbon (%) | 1% | 5% |
| Other Deposits: |  |  |
| 1st Land | 3% light discoloration | trace heavy black lacquer, 2% light discoloration |

|  | Trop-Artic" with Product of Example IV | Trop-Artic" with Lubrizol 925[b] |
| --- | --- | --- |
| 2nd Groove | clean below | trace light amber lacquer |
| 2nd Land |  | clean below |

[a] A registered trademark of the Phillips Petroleum Company representing an SAE 10W-30 oil containing calcium petroleum sulfonate, oxidation inhibitor and viscosity index improver.
[b] Ashless nitrogenous additive made by Lubrizol Corp. of Cleveland, Ohio (concentration of ashless additive set to yield same N concentrate in final blend).

This comparison test shows the improvement obtained by using a product additive of this invention when compared to a commercially available additive.

EXAMPLE V

A mixture of sulfonated petroleum oil (as in Example II) (120 grams), light lube oil blending stock (120 grams) and polyethylenimine (16.8 grams) having an average molecular weight of 1,800 were stirred together at 226°F for 1 hour. Phthalic anhydride (15.0 grams) was added and the temperature increased to 250°F for 45 minutes. The mixture was cooled to room temperature and taken up in cyclohexane, filtered and stripped of cyclohexane.

This product was rated excellent when submitted to a carbon spot dispersancy test. A carbon spot dispersancy test is conducted by stirring 50 milligrams of carbon black into 10 grams of an oil blend containing the candidate additive. A drop of the resulting slurry is then dropped onto a polished Burns Block heated to a temperature of 500°F. The extent to which the carbon black is carried to the extremity of the resulting oil ring is a measure of the dispersancy characteristics of the candidate additive.

EXAMPLE VI

A series of runs was carried out in which a petroleum sulfonic acid having varying concentrations of $SO_2$ present was reacted with an amine and maleic anhydride to form ashless additives for lubricants. The solids content of the additives was determined for each concentration of $SO_2$ in the petroleum sulfonic acid prior to preparation of the additive.

A sulfonated petroleum oil was made from a lubricating oil stock in a manner similar to that described above in Example II. The $SO_2$ content was determined (method KB-59R*) and found to be 0.41 weight percent. A portion of the sulfonated petroleum oil was reacted with tetraethylenepentamine and maleic anhydride. The resulting product was analyzed and found to contain 0.22 weight percent solids content.

*Method KB-59R is a Philips Petroleum Company Procedure for the determination of free $SO_2$ in oil based on the oxidation of $SO_2$ by potassium iodate and titration of the liberated $I_2$ with standard sodium thiosulfate solution.

Another portion of the sulfonated petroleum oil was contacted with nitrogen in order to remove residual amounts of $SO_2$ present in the sulfonated oil. The portion of the sulfonated petroleum oil reduced in $SO_2$ content was reacted with tetraethylenepentamine and maleic anhydride to form the lubricating oil additive. The solids content of the resulting additive was determined after each stripping. The remainder of the sulfonated petroleum oil was subjected to another stripping action to further reduce the $SO_2$ content and a portion of that oil was again reacted with amine and anhydride. The procedure was repeated a number of times until petroleum sulfonated oil having an $SO_2$ content of less than 0.15 weight percent was obtained.

The results of these runs are set forth below in the table.

SUMMARY OF $SO_2$ DATA

| Run | $N_2$ Stripping | % $SO_2$ | % Solids |
| --- | --- | --- | --- |
| 1 | None | 0.41 | 0.22 |
| 2 | 30 minutes | 0.25 | 0.18 |
| 3 | 30 minutes | 0.16 | 0.12 |
| 4 | 60 minutes | 0.13 | 0.10 |
| 5 | 120 minutes | 0.13 | 0.07 |
| 6 |  | 0.13 | 0.06 |

In the above tabulation the sulfonated oil remaining from run 1 which was not used to form the additive was stripped 30 minutes with nitrogen to yield the oil for run 2. Similarly, the oil remaining from run 2 was stripped 30 minutes to yield the oil for run 3, etc. In the above runs, the oil was subjected to nitrogen stripping at a temperature of about 90°F for the period of time set forth in the table. It will also be observed from the above tabulation that reduction of the $SO_2$ content of the petroleum sulfonated oil to a value of about 0.15 and less resulted in an additive having the solids content of less than about 0.12 weight percent which is considered an acceptable level. In view of the reduced solids content of the resulting additive, it is unnecessary to filter the reaction product prior to blending with a lubricant.

I claim:
1. A process for the preparation of an ashless lubricant additive which comprises the steps:
   1. first introducing into a reaction zone a petroleum sulfonic acid formed by sulfonating a high molecular weight, refined petroleum fraction having a viscosity of at least 50 to about 720 SUS at 210°F with a sulfonating agent selected from fuming sulfuric acid and liquid sulfur trioxide under sulfonation conditions and a polyamine selected from the group consisting of
      a. amines of the formula

wherein $x$ equals 2–6 and $y$ equals 1–100, and
      b. a polymer of a 1,2-alkylene imine of the formula

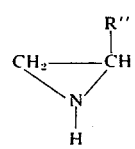

wherein R'' is selected from hydrogen and alkyl radicals having 1–14 carbon atoms, wherein the equivalents of petroleum sulfonic acid employed varies from 1 equivalent of petroleum sulfonic acid per mole of polyamine to 0.75A and the equivalents of the cyclic anhydride employed varies from 0.25 (A–E) to A–E, wherein A is the total equivalents of primary and secondary amines in the quantity of polyamine employed and E is the equivalents of petroleum sulfonic acid employed and allowing said petroleum sulfonic acid and said polyamine to interact, 2. then introducing to the reaction zone a cyclic anhydride of a dicarboxylic acid and allowing it to interact with the product of the interaction between said petroleum sulfonic acid and said polyamine, said cyclic anhydride being represented by the formulas:

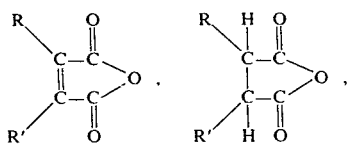

or

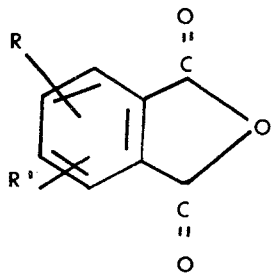

wherein R and R' can be the same or different and are selected from the group consisting of a hydrogen atom and cyclic, acyclic and aromatic hydrocarbyl groups having 1 to 6 carbon atoms to form said ashless lubricant additive.

2. A process according to claim 1 wherein the polyamine is selected from diethylenetriamine, tetraethylenepentamine, and polyethylenimine and the cyclic anhydride is selected from maleic anhydride and phthalic anhydride.

3. A process according to claim 1 wherein the contacting temperature in steps (1) and (2) is from room temperature to about 300°F and steps (1) and (2) are conducted in the presence of solvents selected from hydrocarbons having from 5–12 carbon atoms and lube oil blending stocks having viscosities at 100°F up to about 150 SUS.

4. A process according to claim 1 wherein the ashless additive is recovered in a lube oil stock having a viscosity at 100°F up to about 150 SUS.

5. A process according to claim 1 wherein water formed during the process is recovered by adding an azeotrope forming agent and azeotropically distilling the azeotrope forming agent and water.

6. A process according to claim 5 wherein the azeotrope forming agent is benzene.

7. A process according to claim 1 wherein water formed during the process is recovered by blowing with an inert gas at a temperature from 220° to 300°F.

8. A process according to claim 1 wherein the equivalents of petroleum sulfonic acid employed varies from 0.15A to 0.65A and the equivalents of the cyclic anhydride employed varies from 0.35 (A-E) to 0.75 (A-E), wherein A is the total equivalents of primary and secondary amines in the quantity of polyamine employed and E is the equivalents of petroleum sulfonic acid employed with the further proviso that there be employed at least one equivalent of petroleum sulfonic acid per mole of polyamine.

9. A process according to claim 1 wherein the petroleum sulfonic acid is sulfonated in (1) at a temperature in the range of about 50° to about 200°F with an acid-oil ratio of about 0.1:1 to about 0.7:1 when sulfuric acid is the sulfonating agent and a sulfur trioxide to oil ratio of about 0.02:1 to 0.2:1 when liquid sulfur trioxide is the sulfonating agent.

10. A process according to claim 1 wherein said petroleum sulfonic acid is treated with an inert gas under stripping conditions to remove free $SO_2$ in the oil and the stripping is continued until the petroleum sulfonic acid has been reduced in free $SO_2$ to about 0.15 weight percent or less prior to reacting with the amine.

11. A process according to claim 10 wherein the petroleum sulfonic acid is contacted with nitrogen at a temperature in the range 80°–100°F for up to about 3 hours under stripping conditions until the free $SO_2$ in the oil has been reduced to about 0.15 weight percent or less.

* * * * *